(12) United States Patent
Rometsch

(10) Patent No.: US 7,656,551 B2
(45) Date of Patent: Feb. 2, 2010

(54) METHOD AND APPARATUS FOR ACQUISITION AND ADMINISTRATION OF MEDICAL IMAGE DATA

(75) Inventor: Frank Rometsch, Offenhausen (DE)

(73) Assignee: Siemens Aktiengesellschaft, Munich (DE)

( * ) Notice: Subject to any disclaimer, the term of this patent is extended or adjusted under 35 U.S.C. 154(b) by 830 days.

(21) Appl. No.: 11/367,844

(22) Filed: Mar. 3, 2006

(65) Prior Publication Data

US 2006/0242092 A1    Oct. 26, 2006

(30) Foreign Application Priority Data

Mar. 3, 2005    (DE) .................. 10 2005 009 852

(51) Int. Cl.
*G06F 15/00* (2006.01)
*G06K 9/00* (2006.01)

(52) U.S. Cl. .................... 358/1.15; 382/128

(58) Field of Classification Search ............... 358/1.15, 358/1.14, 1.13, 1.16, 1.18; 382/128, 154, 382/130, 131, 115, 232, 132, 190, 286, 173; 600/407, 437, 442, 427; 709/217, 225, 230, 709/201, 246, 219, 203; 705/2, 3, 7, 11, 705/51; 725/115, 116, 145; 707/1, 3, 9, 707/10, 104.1; 370/462; 715/738

See application file for complete search history.

(56) References Cited

U.S. PATENT DOCUMENTS

2002/0085026 A1 *    7/2002    Bocionek et al. ............ 345/738

\* cited by examiner

*Primary Examiner*—Saeid Ebrahimi Dehkordy
(74) *Attorney, Agent, or Firm*—Schiff Hardin LLP

(57) ABSTRACT

In an apparatus and method for acquisition and administration of medical image data, the apparatus having one or more medical image acquisition modalities for image data acquisition that are to be operated via associated computers, at least one server with an image data storage and at least one workstation computer with an image reproduction device for representation and processing of acquired and/or stored image data; the server and the workstation computer being connected with one another and with the image acquisition modality or image acquisition modalities via a data connection, the ability of a system administrator to get an overview of the system operation is facilitated by the server being configured (relative to the modality) for time-resolved determination of the image data acquisition and administration of associated performance data of the server and/or of the workstation computer, and/or of the data connection, the performance data relating to read and/or write activities at the server, and the server allows graphical representation of the performance data on an image reproduction device.

20 Claims, 6 Drawing Sheets

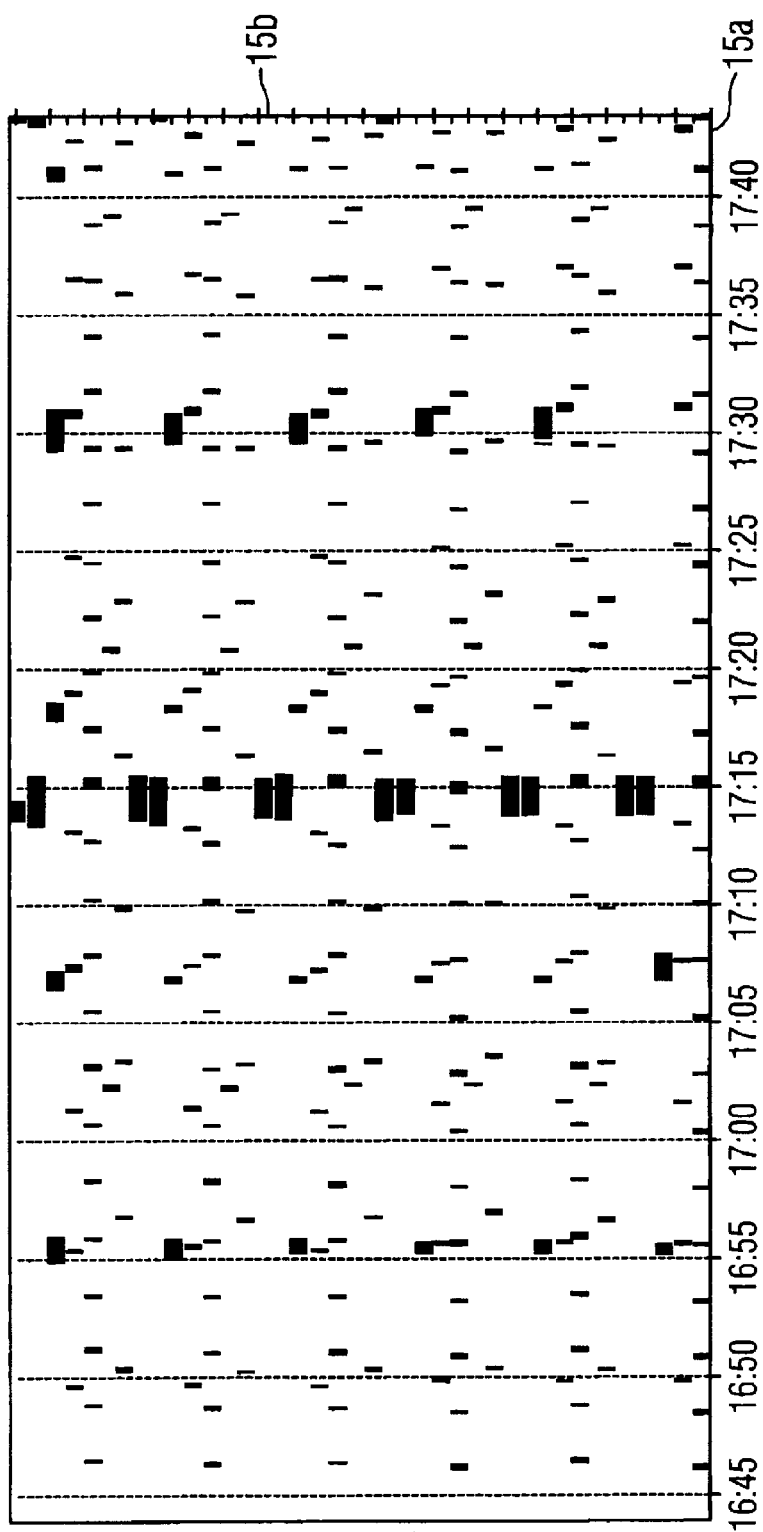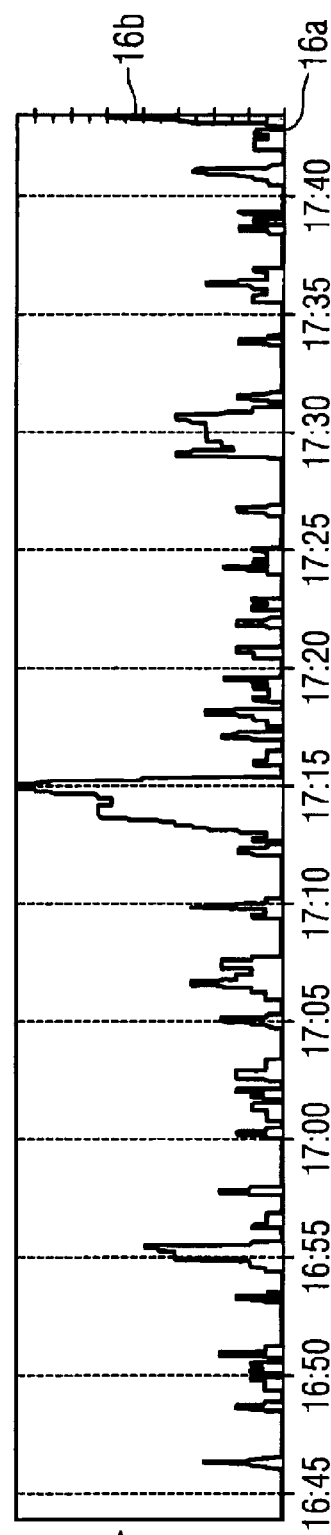
FIG 3A
FIG 3B

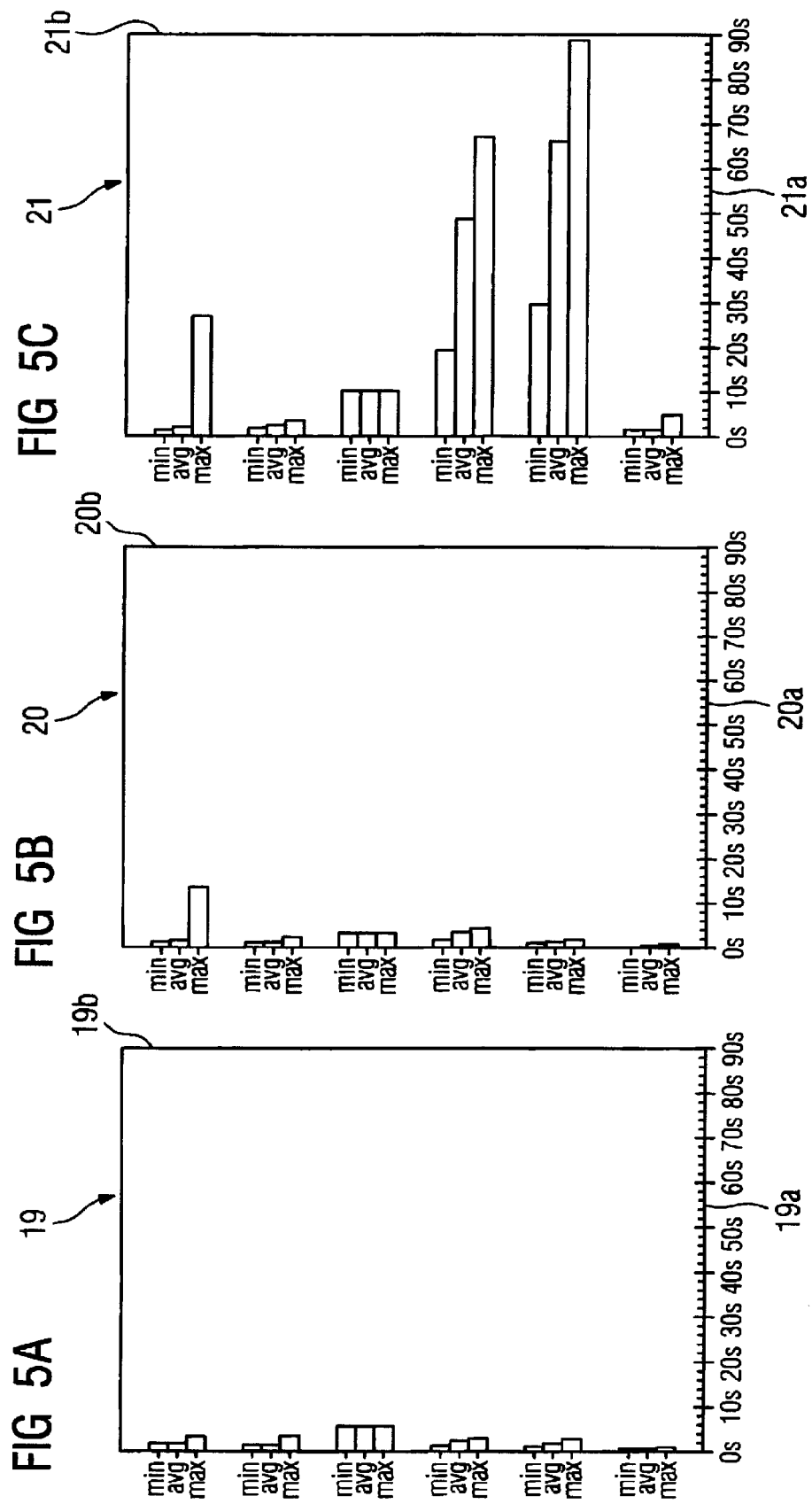

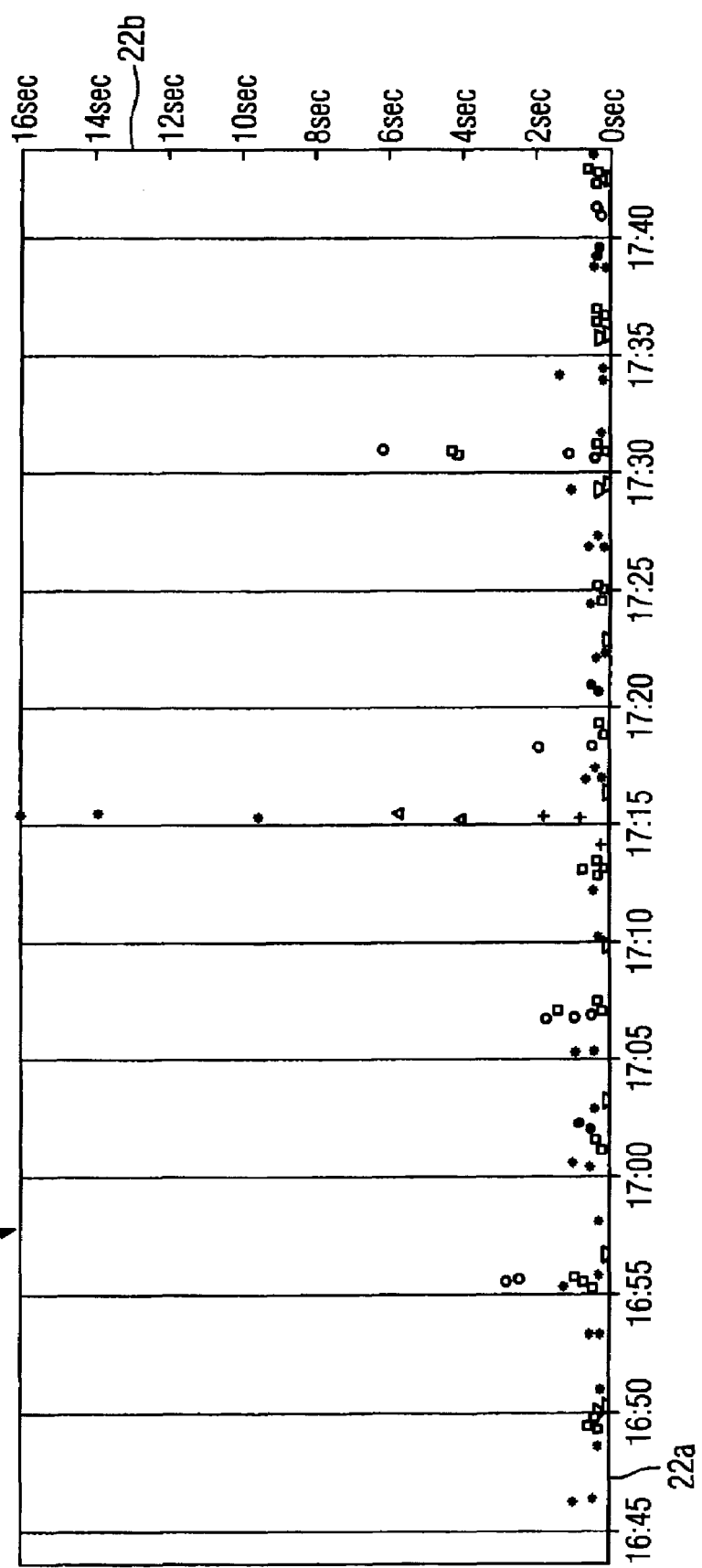

METHOD AND APPARATUS FOR ACQUISITION AND ADMINISTRATION OF MEDICAL IMAGE DATA

BACKGROUND OF THE INVENTION

1. Field of the Invention

The present invention concerns an apparatus for acquisition and administration of medical image data, of the type having one or more medical image acquisition modalities for image data acquisition that are operated by associated computers, a server with an image data storage, and at least one workstation computer with an image reproduction device for representation and processing of acquired and/or stored image data; wherein the server and the workstation computer are connected with one another and with the image acquisition modality or image acquisition modalities via a data connection.

2. Description of the Prior Art

In such apparatuses for acquisition and administration of medical image data, conventionally only a single server is provided with which a number of workstation computers and a number of modalities are normally connected. All information required for image acquisition and administration as well as the actual generated images of the examined patients is stored in the storage unit of the single server. It is therefore very important that the apparatus is operational at all times and is fast enough to be able to quickly process requests on the part of a user of the apparatus and, if applicable, to be able to react quickly to user activities.

Such apparatuses for the image data acquisition and administration, however, are individually configured for almost all customers, for example dependent on the number of hospitals, the type and capacity of the existing image acquisition modalities as well as the relevant doctors. Due to the individual configurations of the apparatuses for image data acquisition and administration, a problem is that these are often too powerful for their particular application, such that unnecessarily high costs arise for the customer. Moreover, an insufficient adaptation to the actual customer requirements can lead to bottlenecks, for example due to insufficient available bandwidth in the network.

The operation of a contemporary apparatus for acquisition and administration of medical image data additionally requires an administrator with special experience, since the service capability of the entire system directly depends on the ability of the administrator to read important data from the system and to correctly interpret them. For example, the administrator must read log files for the correct interpretation of which a great deal of experience is necessary. Additionally it is extremely difficult to recognize the critical components of such an apparatus and to implement targeted improvements.

A medical system architecture with an integrated RIS client of a radiology information system on the console computer of a modality is known from DE 101 54 740 A1. An RIS interface can be used for better planning, monitoring and optimization of the utilization of modalities and all involved resources such as personnel, consumables and the like. Furthermore, a "statistic module" can be used for evaluations. Data can additionally be collected into outcome analyses.

SUMMARY OF THE INVENTION

An object of the present invention is to provide an apparatus for acquisition and administration of medical image data as well as an associated method that are improved to allow a simple check of the operation of an image data device and/or a targeted adaptation to the requirements of a customer.

This object is achieved in accordance with the invention by an apparatus of the type initially described wherein, the server is fashioned (relative to the modality) for time-resolved determination of the image data acquisition and administration of associated performance data of the server and/or of the workstation computer and/or of the data connection, the performance data relating to read and/or write activities at the server, and the server is also fashioned for graphical representation of the performance data on an image reproduction device. The image data acquisition and administration of associated performance data are: the storage activity of one or more image acquisition modalities and/or the storage activator of the at least one workstation computer; and/or the image request activity of the workstation computer; and/or the workstation computer-side load time for individual and/or all images of an acquisition series, and/or a work list, and/or the network traffic entering and/or leaving the server.

In the server of the apparatus, performance data are determined dependent on the modality or modalities that can be, for example, a magnetic resonance system, a CT system or an x-ray device. The performance data can be important for the service capability (thus the reliability or the speed) of the entire apparatus. These performance data can ultimately be traced (ascribed) back to all read and write activities on the server, since the server contains the central image data storage. If images are acquired with a modality such as a CT system or a scintigraph or the like, these images are stored in the image data storage of the server, if applicable after a buffering through an associated computer, or directly. For a subsequent image processing, a new reading of these image data stored on the server is necessary, and if applicable the processed data are in turn stored in the server storage.

These performance data directly or indirectly ascribed to read and write activities are recorded in a time-resolved manner, meaning that the recording time is determined for each datum using a timing element or another time detection device and the recording time is associated with the datum. The performance data are graphically represented on an image reproduction device such as a monitor or a display in order, for example, to provide the administrator (or another interested user) with an intuitively understandable overview of the performance or, respectively, utilization of the apparatus for image acquisition and administration. This image reproduction device can be an image reproduction device of a workstation computer or also a reproduction device directly associated with the server that is normally used only by the administrator.

Specific problems related to the medical image data acquisition and administration can be quickly and clearly detected as a consequence of the targeted collection and extraction of data representing a measure for the performance of the apparatus, which data are directly related to the specific operation of the apparatus (namely the image data acquisition). It is thereby possible to continuously check the image data apparatus during the operation. Given a step-by-step or module-by-module construction of such an image data and image administration apparatus, it is furthermore possible to adapt the apparatus in a targeted manner to the requirements of a customer who, for example, operates one or more hospitals with different capacities. The administrator automatically receives the performance data that is needed, so a laborious gathering of such data is avoided. Through the graphical representation, the interpretation of these data is additionally made significantly easier in comparison to a conventional numerical display.

In a further embodiments the image data acquisition and administration of associated performance data are: the storage activity of one or more image acquisition modalities and/or the storage activity of the at least one workstation computer, and/or the image request activity of the workstation computer, and/or the workstation computer-side load time for individual and/or all images of an acquisition series, and/or a work list, and/or the network traffic entering and/or leaving the server. All of these performance data can ultimately be ascribed back to read and write activities at the server.

The storage activity of the modalities thereby indicates how many storage events or procedures are implemented on the image data storage of the server by one or more modalities at specific times. Alternatively or in parallel, the storage volume (thus the size of the images that were acquired by the modalities and must now be stored on the server) can be specified. The storage activity of at least one workstation computer can likewise be determined and graphically represented when images previously accessed from the server are processed and stored again. The image request activity of the workstation computer specifies how many images, images of which size or which total volume are requested by the workstation computer for viewing or processing.

Furthermore, it can be informative to have an overview of the time that it takes until an individual image is loaded on a workstation computer. A further measure for the performance of the acquisition and administration apparatus is the load time for all images of an acquisition series. The length of such acquisition series significantly varies with the respective modality since the modalities acquire different amounts of images of different sizes. Furthermore, the load time for a work list can be determined and displayed in which the acquisitions to be implemented or already implemented for a specific modality or for a patient are, if applicable, indicated with preview images. The network traffic that arrives at the server or exits from the server over the data connection can indicate bottlenecks in the bandwidth and points of the respectively selected network configuration currently in use that will fail in the near future. The data connections between the server and the modalities or between the server and the workstation computer thus can be specifically improved.

In accordance with the invention the time span for which the determination and/or graphical representation of the performance data ensues can be selected by the user. For example, the administrator can establish that a performance data determination is implemented over a time span of multiple hours, or days. For clarity a graphical representation should be implemented only for small time spans such as, for example, an hour, within the total time span. The time spans for the data determination or representation can also be specified in the form of repeatedly recurring intervals that, for example, encompass the operating times of the modalities, or the work times of the technical personnel or specific days within a month that are sought in a random sample for a performance evaluation. For data determination, timing elements can be used that are operated, for example, pulse-controlled, for example dependent on a specific provided check pulse or interference information. A clocked operating mode is likewise possible, such that the determination or representation is reactivated and ended dependent on predetermined clock pulses.

Preferably, the apparatus is configured for association of the performance data with specific points in time. The administrator of the apparatus thus can associate, for example, performance peaks or valleys with specific hours or data, so that a determination of the causes of such special appearances in the time curve of the determined performance data is distinctly simplified.

In an embodiment of the invention the apparatus is configured for graphical representation of the performance data by means of a browser program. Currently a standard browser is installed on nearly every computer, such that a graphical representation for which only an executable browser program is required offers the advantage that it can be called up nearly everywhere. The administrator thus can retrieve the performance data (protected, if applicable, by a specific password) not only at the image reproduction device that is associated with the server but also at workstation computers to which the user is called in the case of problems or at which the user undertakes maintenance tasks. The graphical representation can additionally be made accessible to interested or authorized users without an instruction in a specific program being necessary, and without a special further display software having to be installed.

The graphical representation by means of the browser program can include a start page via which specific performance data to be displayed (in particular the type of the data and/or an associated modality and/or the time window of the representation) can be selected. Via such a general start page, a structured overview about the graphical representation possibilities is provided to the user of the graphical representation (who will normally be an administrator), such that a specific selection of the data relevant for him or her and the representations of the selected data is possible. The selection can ensue via specific (in particular labeled) buttons or with the use of check boxes that are associated with specific data types or modalities. Furthermore, the user can select the time window of the representation, for example as a representation of the data of the past hour or of a longer or shorter time span. A defined specification of the point in time with which the representation starts as well as the point in time with which it ends is likewise possible.

The representation of the selected performance data can ensue on the start page and/or in new browser windows. The selected performance datum for the selected time window can be shown, for example, below the area in which the selection possibilities that are available are displayed. If further performance data are selected for display, these can be shown if applicable in separate graphics below the first representation. Alternatively, it is possible that the previous representation is cleared given a new selection. If applicable, a user can specifically select such clearing, by a button or the like with a reset function being provided in the start page (programmed, for example, in HTML). A programming is likewise possible such that a new window that displays this graphical representation is opened upon a selection of a specific representation that is, if applicable, to be confirmed via a confirmation button. If the user desires a representation of further performance data and selects this on the start page in the browser program, the selected data are likewise shown in their own new windows. The windows of earlier representations can be retained or cleared.

According to the invention, the performance data can be individually displayable for each image acquisition modality given multiple image acquisition modalities, and/or can be individually displayable for each workstation computer given multiple workstation computers, and/or can be displayable in accumulated form for all image acquisition modalities and/or all workstation computers. Given an individual display for each image acquisition modality, characteristics of the operation of this specific modality are apparent at a glance in the graphical representation. For example, using the write processes of this modality on the image data storage, the examination frequency prevalent at this modality can be reconstructed. For example, it can be additionally detected whether only small data sets are transported, or whether short access times exist, or whether it is reasonable to better connect this modality if, for, example, it is seen that write events or procedures must be frequently repeated since errors occur. Given a breakdown according to the workstation computers, it can likewise be detected when, for example, problems exist in a specific section of the network topology. The workstation computers can additionally be specially customized to the requirements of the respective user, for example depending on which user retrieves images of which size how often from the image data storage and, if applicable, processes them on the workstation computer. In the case of frequent access, the load times and the storage times thereby observed are of particular importance.

An accumulated representation allows a fast overview of the performance capability of the overall system. It can thus be quickly recognized whether, for example, it is reasonable to further upgrade the system or whether the present capacities are actually sufficiently utilized. Local bottlenecks that have significant effects on the overall system can be specifically detected and remedied by a combination of the individual representation and the accumulated representation.

In another embodiment of the invention the apparatus has separate modules for determination of the performance data and the graphical representation. The underlying concept is that it is possible to install an independent module on the computer of an inventive apparatus, which independent module implements only the tasks of the data determination, thus the collection of all performance-related information that are relevant for the image data acquisition or administration. Such a data collection can ensue continuously in the background. Files can thereby be generated that are, if applicable, subjected to update operations continuously or in specific time spans. These files can be read by the module for graphical representation, which is independent from the determination module, and be processed for the representation.

The apparatus for determination of the data of the module for determination of the performance data can be provided at external systems on which the module for graphical representation is executable. It is thus possible to achieve a graphical representation of the data collected within the apparatus with the determination module, this graphical representation ensuing on external systems on which no data collection or determination has occurred. For example, an evaluation by external specialists is thus possible in a significantly easier manner; the apparatus must merely transmit the raw data of the determination module to the computer of such an external specialist. The raw data are less extensive than the data to be processed into a graphic that the module generates for graphical representation. Conversely, only the module for determination of the performance data is necessary for an inventive apparatus. Preparation for an administrator into a structured performance report thus does not necessarily have to ensue on site.

Furthermore, the device for determination and graphical representation of the total CPU load and/or the CPU load dependent on the image acquisition and administration and/or the total running processing and/or processes associated with the image acquisition and/or administration, can be configured for the computer of the apparatus. This involves data that give a general overview of the activities of a computer system. It can be meaningful to consider the overall CPU load of individual computers or all computers of the apparatus in order, for example, to detect problems that have effects on the image acquisition and administration, but are not directly connected with these or caused by these. The CPU of a workstation computer thus could already be loaded by an over-dimensioned (oversized, over-designed) operating system, such that loading of images from the storage of the server cannot ensue in a justifiable amount of time. The CPU load that is dependent on the image acquisition and administration also shows whether, for example, an inadequate design is present. The overview of the running processes can also supply, for example, indications of whether current unnecessary processes impair the image processing or whether processes directly connected with the image data acquisition or administration require more capacity than is available, or for example are not properly terminated. Not only performance data that are to be associated with the image data acquisition and administration can be specifically determined and graphically prepared with the inventive apparatus, but also further data that are generally of importance for the performance of a computer system can be collected and simply checked using the graphical representation.

The invention additionally concerns a method for acquisition and administration of medical image data that are acquired with one or more image acquisition modalities to be operated via associated computers, wherein the image data are stored in an image data storage of a server and the acquired and stored image data are represented and/or processed by at least one workstation computer with an image reproduction device, and wherein the server and the workstation computer are connected with one another and with the image acquisition modality or image acquisition modalities via a data connection. In the inventive method, relative to the modality, performance data of the server and/or the workstation computer and/or the data connection that are associated with the image data acquisition and administration (which performance data concern read and/or write activities on the server) are determined in a time-resolved manner and are graphically represented on an image reproduction device. The storage activity of the one or more image acquisition modalities and/or the storage activity of the at least one workstation computer, and/or the image request activity of the workstation computer, and/or the workstation computer-side load time for individual and/or all images of an acquisition series, and/or a work list, and/or the network traffic entering and/or leaving the server, are determined and represented as performance data associated with the image data acquisition and administration.

The storage activity of the one or more image acquisition modalities and/or of the at least one workstation computer, and/or the image request activity of the workstation computer, and/or the workstation computer-side load time for individual and/or all images of an acquisition series, and/or a work list, and/or the network traffic entering and/or leaving the server, are thus determined and represented as performance data associated with the image data acquisition and administration. All of these activities are ultimately read and/or write activities at the image data storage of the server that, if applicable, can be divided into a storage unit for storage for shorter time spans and a storage unit for storage over longer time spans. The network traffic that arrives at the server and/or exits the server over the data connections can be divided, if applicable, according to the associated interfaces. Storage activities can likewise additionally be divided with regard to specific storage units or fixed disks. Overall a comprehensive overview thus results of the data that are necessary for the image acquisition and administration in the medical field.

In an embodiment of the inventive method, the graphical representation of the performance data can ensue by means of a browser program. In particular, specific performance data to be represented (such as the type of the data and/or an associated modality and/or the time window of the representation) are selected by the user via a start page.

The operating mode of the one or more image acquisition modalities and/or of the server and/or of the at least one workstation computer can be emulated by a computerized simulation. This enables the use of the inventive method in a phase when a decision should be made about the design or a further upgrade of an apparatus for image data acquisition and administration, since the necessary capacities thus can be specifically predicted. Such a simulation also can serve to adjust an existing apparatus in order to find bottlenecks or to detect problems without, for example, impairing the actual clinical operation.

In the inventive method, given a number of image acquisition modalities and/or workstation computers, the performance data can be individually displayed for each image acquisition modality and/or each workstation computer and/or can be displayable in accumulated form for all image acquisition modalities and/or all workstation computers. Furthermore, data determined with a module for determination of the performance data can be transmitted to external systems, and the performance data can be displayed by means of a module for graphical representation that is executable on external systems.

DESCRIPTION OF THE DRAWINGS

FIGS. 3A, and 3B respectively illustrate time-resolved representations of the image request activities of a number of workstation computers in accordance with the invention.

FIGS. 5A, 5B and 5C respectively show representations of the load times for various workstation computers in accordance with the invention.

FIG. 6 shows a time-resolved representation of the response times of various modalities in accordance with the invention.

DESCRIPTION OF THE PREFERRED EMBODIMENTS

Figure 1:
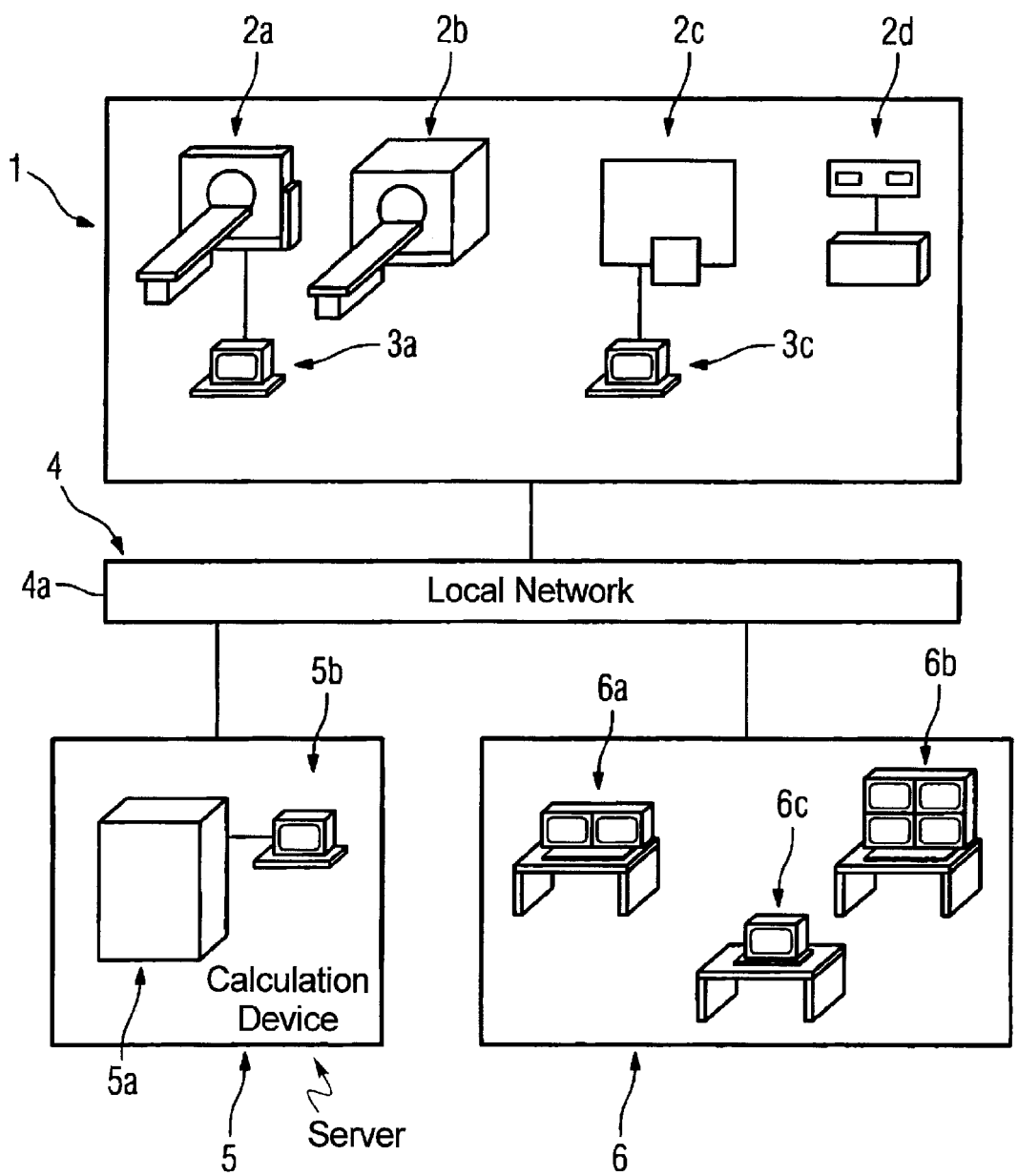
FIG. 1 shows an inventive apparatus for acquisition and administration of medical image data.

FIG. 1 shows an inventive apparatus 1 for acquisition and administration of medical image data. The apparatus 1 has various medical image acquisition modalities 2a through 2d that are represented in part with associated computers 3a and 3c for their operation. Each computer 3a and 3c has a monitor and an input device via which the image acquisitions to be effected can be established, for example, by selection of an acquisition series.

The image acquisition modality 2a is a CT system, the modality 2b is a magnetic resonance device, 2c is an x-ray device and 2d is an ultrasound device. The image acquisition modalities 2a through 2d are connected with a server 5 as well as various workstation computers 6 via a data connection 4 that is fashioned as a local network with a switch that, in the example, is indicated by a box with the reference character 4a. The server 5 as well as the workstation computers 6 (which include 6a, 6b and 6c) is in turn connected with one another via the data connection 4. The connection of the individual computers to the data connection 4 is hereby not shown in detail for clarity. The workstations 6a, 6b and 6c are equipped differently, with the hardware of each having appropriately adapted to the particular application field. A technical employee in a hospital, whose task is the preparation of images of one or more image acquisition modalities 2a through 2d so that these can be forwarded to the appropriate treating doctors, thus requires more computer capacity than a doctor who only occasionally includes image data of a specific examination modality into his examination report.

The server 5 possesses a storage and calculation device 5a and an image reproduction device 5b with an input device. All image data acquired with the image acquisition modalities 2a through 2d are centrally stored in the image data storage of the storage and calculation device 5a of the server 5. If these image data should be processed at individual workstation computers 6a through 6c, they are loaded onto the workstation computer after a request and buffered if applicable in order to ultimately be stored centrally again in the image data storage of the server 5, and thus be generally accessible for authorized users.

With the apparatus 1, an administrator of the inventive apparatus 1 who wants to check the performance of the image data acquisition and administration system has the possibility to view the relevant performance data (which are centrally collected by the server 5 that has access to all processes in connection with the image data acquisition in the apparatus 1) in a graphical representation at the image reproduction device 5b. For this purpose, these performance data are displayed in a browser program with a corresponding start page for selection of the data to be represented. Via an appropriate log-in, the administrator or authorized users can access the graphical representation of these performance data, even at the workstations 6a through 6c.

The performance data are ultimately to be ascribed back to read and write activities at the server 5, since all image data are stored in the storage and calculation device 5a for a shorter or longer time depending on the type of the usage or dependent on data protection rules. For example, the requests that come from individual workstations 6a or 6b can be displayed as performance data determined by the server.

Not shown here is a connection of the local network to other external systems or, respectively, other networks in order to thus transmit files of a module for performance data determination, at which the transmitted data are then displayed in an intuitively comprehensible graphic at a respective external system with the aid of a module for graphical representation that is portably programmed. Not only can the administrator (who is directly linked into the local network of the apparatus for acquisition and administration of medical image data) check the performance data, but so can an external specialist, or an administrator who is not actually present.

Figure 2:
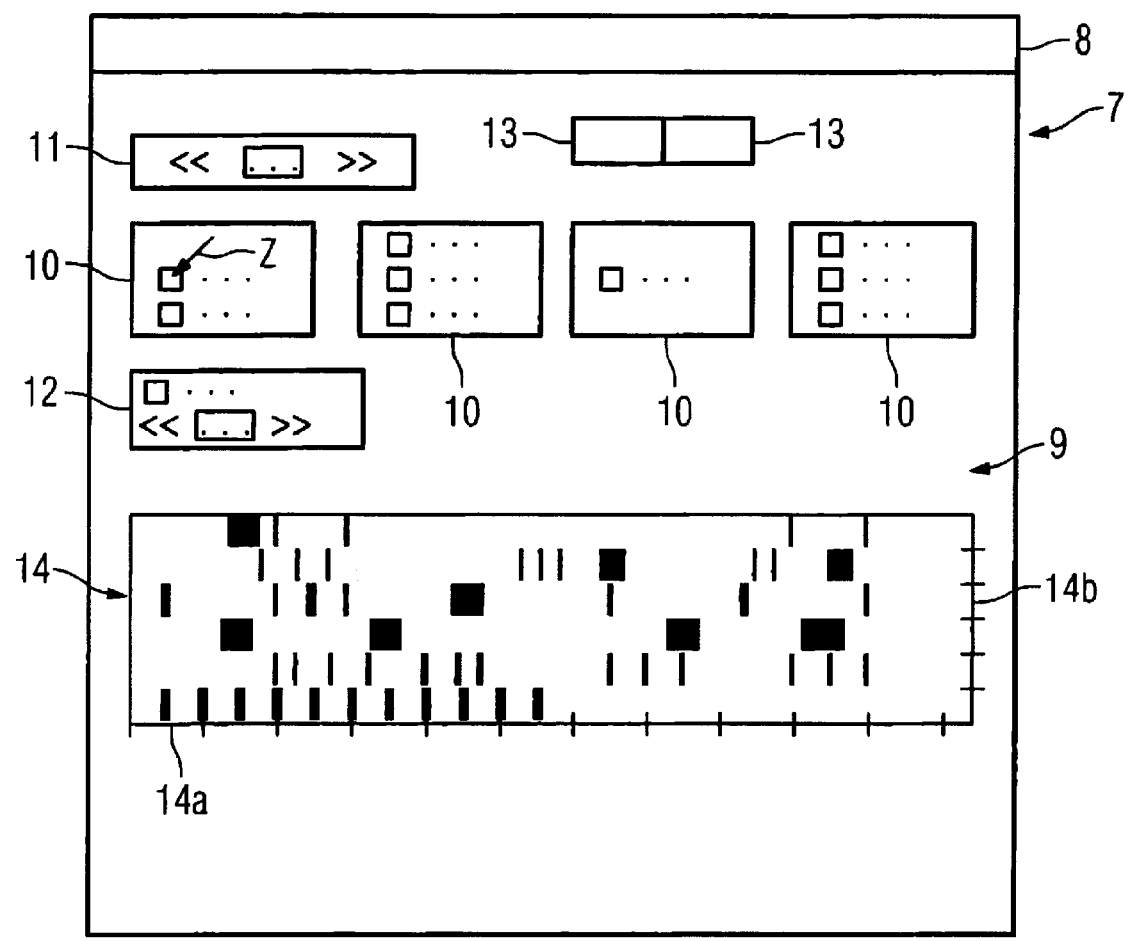
FIG. 2 is a representation of performance data in the inventive method.

FIG. 2 shows a representation of performance data given an inventive method. The representation ensues in a browser window 7 with a menu bar 8 via which specific functions or, respectively, URLs can be selected. If, in the inventive method, a start page 9 for the graphical representation of the performance data is called with the aid of the menu bar 8, various selection and information fields 10 appear that offer an overview of the available performance data that have been collected by means of a determination method. By means of a further selection field 11, a user can select the time span or, respectively, the points in time that should form the basis of the graphical representation. A further selection field 12 serves for the selection of various modalities as well as modality-specific functionalities. The settings can be reset or the representations of the individual fields can be masked [blanked] with the aid of the function fields 13.

The user (normally the administrator) who is interested in specific performance data that are associated with the image data acquisition and administration now selects one of the check boxes of the selection and information fields 10 with the aid of the mouse pointer Z. This check box is associated with a specific performance datum that is subsequently (after the time span to be represented was previously specified in the selection field 11) displayed on the start page below the fields in the representation 14. In the present case, the user has selected a representation 14 of the storage activities of the various modalities. The time span selected with the aid of the selection field 11 is correspondingly shown in the representation on the horizontal axis 14a, while the individual modalities are plotted on the vertical axis 14b. With the aid of the graphical representation 14, the user can recognize that the storage activities of the modalities in the considered time span were very different. For example, in the first half of the time span respectively only short storage activities in the image data storage of the server forming the basis of the method were conducted with the modality plotted at the bottom. In contrast to this, in the considered time span the modality plotted at the top has conducted one storage process that took a longer time span, in addition to a few very short storage processes. The administrator can thus quickly detect possible bottlenecks, and the computers that form the basis of the inventive method can be specifically adapted to the actual present requirements.

Given selection of further performance data by clicking with a mouse pointer Z, these appear below the representation 14 insofar as the reset function was not previously triggered with the aid of the function field 13.

FIGS. 3A and 3B show respective time-resolved representations of the image request activities of a number of workstation computers. In FIG. 3A an individual representation 15 is thereby selected in which a time span of one hour with established start and end time points is specified on the horizontal axis 15a. The various workstation computers of the inventive apparatus are specified on the vertical axis 15b. Different image request activities of the individual workstation computers result from the representation, to the effect that predominantly or exclusively short activities came from a few computers while other computers have executed only one request activity in the underlying time span, which one request activity did, however, take a longer time span. The reason for this can be seen to be that the workstations are operated by different personnel circles who merely process the images of a specific modality or, as is the case for a doctor who only has to create a report, request only reduced versions of the image data. The administrator can additionally recognize at a glance when specific request peaks have occurred and draw conclusions from this with regard to possible bottlenecks.

The representation 16 of FIG. 3B shows the accumulated image request activities for all workstation computers for the same time span (plotted on the horizontal axis 16a), such that now the number of the activities that come from all computers in total is plotted on the vertical axis 16b. The high activity around the point in time 17:15 is clearly recognizable. From this accumulated representation, the administrator can at a glance make assertions with regard to the utilization of the overall system. For example, if it leads to delays in the image request, an upgrade of the network capacity or a temporal equalization of the accesses is thus necessary.

Figure 4A:
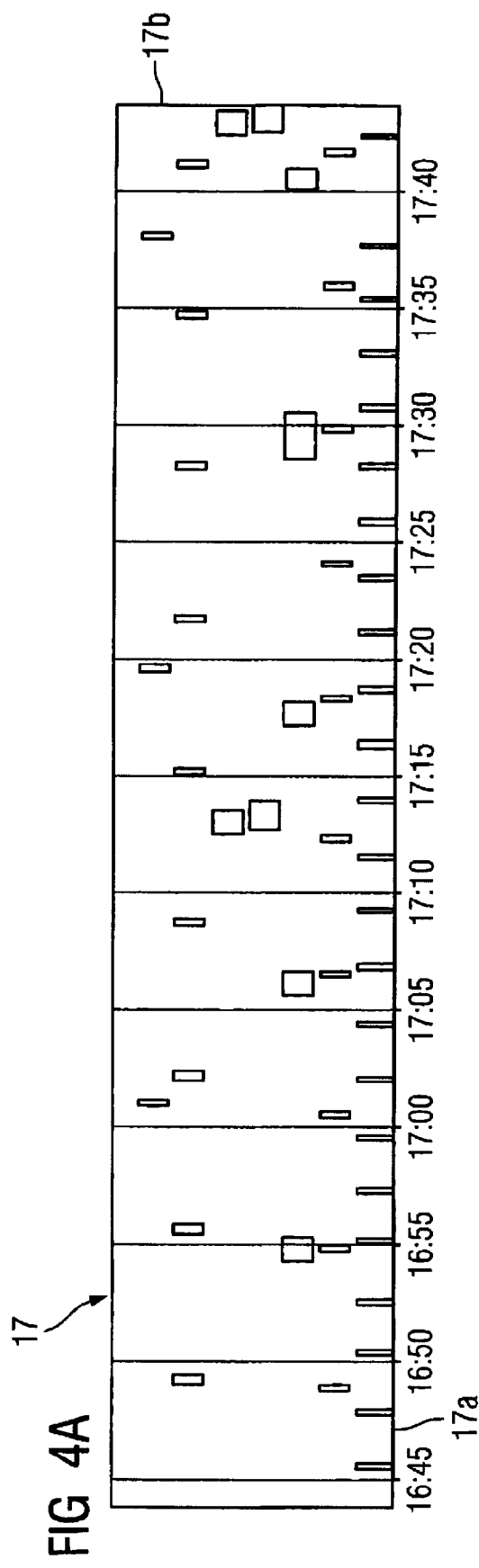
FIGS. 4A and 4B respectively illustrate time-resolved representations of the storage activities of a number of modalities in accordance with the invention.
Figure 4B:
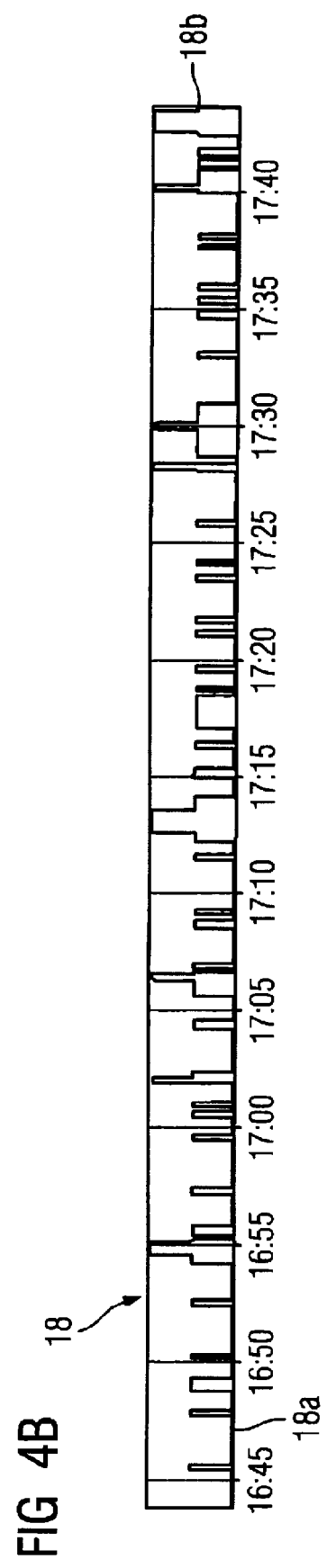

FIGS. 4A and 4B respectively show time-resolved representations of the storage activity of a number of modalities, whereby an individual representation 17 is shown in FIG. 4A, again for a time span of one hour as it is plotted on the horizontal axis 17a. The individual modalities that store the acquired images in the image data storage of the server are plotted on the vertical axis 17b. Since image data sets of different sizes or, respectively, acquisition series or different lengths are acquired with different modalities, the storage activities of the modalities are very different. The storage activities additionally depend on the utilization of the respective modality, thus the frequency with which examinations are conducted. For example, dependent on this graphic it can be determined how much storage space in the image storage of the server should be associated with a specific modality.

By means of the accumulated representation of FIG. 4B, in which the number of the activities is plotted on the vertical axis 18b over the time span represented on the horizontal axis 18a, it can be determined how many storage activities run simultaneously and how long each lasts. For example, bottlenecks can be detected and, if applicable, rules can be provided that regulate the priority of the storage activities of individual modalities.

The load times for various workstation computers are respectively shown in FIGS. 5A, 5B and 5C.

In the representation 19 of FIG. 5A, the load time is specified in seconds on the horizontal axis 19a while the vertical axis 19b is divided according to the associated workstation computers. The representation 19 refers to a specific examination modality, whereby in the present case the time is considered that is required for loading of the work list that determines an acquisition sequence of the modality. The minimal, average and maximal load times that were determined for the examination time span are thereby specified for each workstation computer that is plotted on the vertical axis 19b.

For the same workstation computers plotted on the respective vertical axes 20b and 21b, the representations 20 and 21 of FIGS. 5B and 5C show the minimum, average and maximal load times that were required for loading of the first image of a series acquired with the associated modality as well as, in the case of FIG. 5C, for loading of the entire series. The horizontal axes 20a and 21a are likewise divided as in FIG. 5A. Bottlenecks that are present at individual workstation computers can be specifically tracked down via a comparison of the load times. For example, the workstation computer shown at the bottom quickly loads the work list, the first image as well as all images of the series, with hardly any interferences, as is clear from the low maximum time. The computer plotted, just above this in particular shows a large time requirement upon loading of the complete image series, such that under the circumstances the processing of images is unnecessarily delayed.

Lastly, a time-resolved representation 22 of the response times of various modalities (with which different symbols are respectively associated here) is shown in FIG. 6. The underlying time span is plotted on the horizontal axis 22a of the representation 22 while the response time in seconds is specified on the vertical axis 22b. From this graphical representation, it is immediately apparent to the administrator that the response times for the most part lie under one second. Long response times of over eight seconds occur only at a single modality, such that this possible bottleneck can be specifically checked.

By means of the inventive apparatus and the associated method, the administrator or a user thus is able to collect and to graphically represent specific performance data for the medical image data acquisition, such that a fast overview of the performance capability of the system, or of existing over-capacities and under-capacities, is obtained. An upgrade can ensue in a targeted manner and the work in connection with the medical image acquisition can be optimized independent of special capabilities of the responsible administrator.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for acquisition and administration of medical image data, comprising:
    at least one medical imaging modality that acquires medical image data, said medical imaging modality comprising an operating computer that operates the medical imaging modality;
    a server having an image data storage, in which said medical image data acquired by said medical imaging modality is stored;
    at least one workstation computer having an image reproduction device, said workstation computer processing and representing, via said image reproduction device, medical image data from said image data storage of said server or medical image data supplied directly from said medical imaging modality;
    a data connection placing said operating computer, said server and said workstation computer in data communication with each other;
    said server being configured for time-resolved identification of the acquisition of said medical image data and for administration of associated performance data for at least one of said server, said workstation computer and said data connection, said performance data comprising activities of said server selected from the group consisting of read activities and write activities, and said performance data being selected from the group consisting of a storage activity of said at least one medical imaging modality, storage activity of said at least one workstation computer, image request activity of said workstation computer, a loading time at said workstation computer for individual medical images, a loading time at said workstation computer for medical images in a series, network traffic entering said server and network traffic exiting said server; and
    said server having a server image reproduction device and said server being configured to represent said performance data at said server image reproduction device.

2. An apparatus as claimed in claim 1 comprising a user interface in communication with said server, said user interface allowing entry by a user of an instruction for representing said performance data, said instruction being selected from the group consisting of a time span and a designated graphical representation type.

3. An apparatus as claimed in claim 1 wherein said server associates said performance data with specific points in time relative to acquisition of said medical image data.

4. An apparatus as claimed in claim 1 wherein said server represents said performance data at said server image reproduction device according to a browser program executed by said server.

5. An apparatus as claimed in claim 4 wherein said server, according to said browser program, represents said performance data at said server image reproduction device in a graphical representation comprising a start page allowing selection by a user of specific data, among said performance data, to be represented.

6. An apparatus as claimed in claim 5 wherein said server, according to said browser program, represents the selected performance data at a location selected from the group consisting of said start page, and a new browser window displayed at said server image reproduction device.

7. An apparatus as claimed in claim 1 wherein said server, via said data connection, also allows representation of said performance data at said image reproduction device of said workstation computer or at an image reproduction device connected to said operating computer.

8. An apparatus as claimed in claim 1 wherein said server comprises a first module for determination of said performance data and a second module for graphical representation of said performance data, said first and second modules being separate from each other.

9. An apparatus as claimed in claim 8 wherein said server is configured to transmit said performance data determined in said first module to an external system, having a duplicate of said second module, to allow graphical representation of said performance data at said external system.

10. An apparatus as claimed in claim 1 wherein said apparatus has a total computer load, and wherein at least one of said operating computer and said workstation computer calculates at least one of said total computer load, a portion of said total computer load dependent on acquisition of said medical image data, a portion of said total computer load dependent on a procedure executed by any of said medical imaging modality, said workstation computer and said server, for graphical representation with said performance data.

11. A method for acquisition and administration of medical image data, comprising the steps of:
    acquiring medical image data using at least one medical imaging modality, said medical imaging modality comprising an operating computer that operates the medical imaging modality;
    storing said medical image data acquired by said medical imaging modality in an image data storage;
    processing said medical image data at at least one workstation computer having an image reproduction device, and representing, via said image reproduction device, medical image data from said image data storage of said server or medical image data supplied directly from said medical imaging modality;
    placing said operating computer, said server and said workstation computer in data communication with each other via a data connection;
    in said server, making a time-resolved identification of the acquisition of said medical image data and for administration of associated performance data for at least one of said server, said workstation computer and said data connection, said performance data comprising activities of said server selected from the group consisting of read activities and write activities, and said performance data being selected from the group consisting of a storage activity of said at least one medical imaging modality, storage activity of said at least one workstation computer, image request activity of said workstation computer, a loading time at said workstation computer for individual medical images, a loading time at said workstation computer for medical images in a series, network traffic entering said server and network traffic exiting said server; and
    representing said performance data at a server image reproduction device of said server.

12. A method as claimed in claim 11 comprising allowing an entry, via a user interface in communication with said server, of an instruction for representing said performance data, said instruction being selected from the group consisting of a time span and a designated graphical representation type.

13. A method as claimed in claim 11 comprising, said server, associating said performance data with specific points in time relative to acquisition of said medical image data.

14. A method as claimed in claim 11 comprising representing said performance data at said server image reproduction device according to a browser program executed by said server.

15. A method as claimed in claim 14 comprising, according to said browser program, representing said performance data at said server image reproduction device in a graphical representation comprising a start page allowing selection by a user of specific data, among said performance data, to be represented.

16. A method as claimed in claim 15 comprising, according to said browser program, representing the selected performance data at a location selected from the group consisting of said start page, and a new browser window displayed at said server image reproduction device.

17. A method as claimed in claim 11 comprising, via said data connection, also allowing representation of said performance data at said image reproduction device of said workstation computer or at an image reproduction device connected to said operating computer.

18. A method as claimed in claim 11 comprising forming said server as a combination of a first module for determination of said performance data and a second module for graphical representation of said performance data, said first and second modules being separate from each other.

19. A method as claimed in claim 18 transmitting said performance data determined in said first module to an external system, having a duplicate of said second module, to allow graphical representation of said performance data at said external system.

20. A method as claimed in claim 11 wherein said apparatus has a total computer load and, in at least one of said operating computer and said workstation computer, calculating at least one of said total computer load, a portion of said total computer load dependent on acquisition of said medical image data, a portion of said total computer load dependent on a procedure executed by any of said medical imaging modality, said workstation computer and said server, for graphical representation with said performance data.

* * * * *